United States Patent [19]
Howells et al.

[11] Patent Number: 5,874,616
[45] Date of Patent: Feb. 23, 1999

[54] PREPARATION OF BIS (FLUOROALKYLENESULFONYL) IMIDES AND (FLUOROALKYSULFONY) (FLUOROSULFONYL) IMIDES

[75] Inventors: Richard D. Howells, Dellwood; William M. Lamanna, Stillwater; Alan D. Fanta, Minneapolis; Jennifer Waddell, Burnsville, all of Minn.

[73] Assignee: Minnesota Mining and Manufacturing Company, St. Paul, Minn.

[21] Appl. No.: 577,425

[22] Filed: Dec. 22, 1995

Related U.S. Application Data

[63] Continuation-in-part of Ser. No. 398,859, Mar. 6, 1995, Pat. No. 5,514,493.

[51] Int. Cl.$^6$ .................................................. C07C 303/38
[52] U.S. Cl. .............................. 564/82; 562/822; 564/83
[58] Field of Search .......................... 562/822; 564/82, 564/83

[56] References Cited

U.S. PATENT DOCUMENTS

| 385,299 | 4/1888 | Hentrich et al. | 564/82 |
|---|---|---|---|
| 2,732,398 | 1/1956 | Brice et al. | 260/503 |
| 3,336,382 | 8/1967 | Pearson et al. | 562/822 |
| 3,423,299 | 1/1969 | Loree | 204/59 |
| 3,476,753 | 11/1969 | Hansen | 260/247.1 |
| 3,542,864 | 11/1970 | Koshar | 260/543 |
| 3,623,963 | 11/1971 | Voss et al. | 204/59 |
| 3,776,960 | 12/1973 | Koshar et al. | 260/607 A |
| 3,951,762 | 4/1976 | Voss et al. | 204/59 F |
| 4,505,997 | 3/1985 | Armand et al. | 429/192 |
| 5,072,040 | 12/1991 | Armand | 564/82 |
| 5,256,821 | 10/1993 | Armand | 564/82 |
| 5,273,840 | 12/1993 | Dominey | 429/192 |
| 5,318,674 | 6/1994 | Behr et al. | 204/59 F |
| 5,414,117 | 5/1995 | Armand et al. | 562/828 |
| 5,414,120 | 5/1995 | Pohmer et al. | 564/82 |
| 5,446,134 | 8/1995 | Armand et al. | 534/558 |
| 5,463,005 | 10/1995 | Desmarteau | 526/240 |

FOREIGN PATENT DOCUMENTS

| 2096816 | 11/1993 | Canada . | |
|---|---|---|---|
| 0 576 225 | 12/1993 | European Pat. Off. . | |
| 2 683 524 | 5/1993 | France . | |
| 2239817 | 2/1974 | Germany . | |
| 1 309 621 | 3/1973 | United Kingdom | C07C 143/72 |
| WO95/26056 | 9/1991 | WIPO . | |
| WO 93/16988 | 9/1993 | WIPO . | |

OTHER PUBLICATIONS

Foropoulos, J., et al., "Synthesis, Properties, and Reactions of Bis ((trifluoromethyl) sulfonyl) Imide, $(CF_3SO_2)_2NH^1$," *Inorganic Chemistry*, vol. 23, (1984), pp. 3720–3723.

DesMarteau, "Novel Perfluorinated Ionomers and Ionenes," *J. Fluorine Chem.*, vol. 72, (1995) pp. 203–208.

Hu, et al., "Synthesis of Perhaloalkanesulfonyl Halides and Their Sulfonimide Derivatives," *Inorg. Chem.*, vol. 32, (1993) pp. 5007–5010.

Hudlicky, M., *Chemistry of Organic Fluorine Compounds*, 2nd ed., PTR Prentice Hall (N.Y.) pp. 73–76.

Huang, "The Recent Progress of Fluoroorganic Chemistry in China," *J. Fluorine Chem.*, vol. 32, (1986) pp. 179–195.

Krutak, et al., "Chemistry of Ethenesulfonyl Fluoride. Fluorosulfonylethylation of Organic Compounds," *J. Organic Chem.*, vol. 44, No 22, (1979) pp. 3847–3858.

Mohtasham et al., "β–Fluorosultones: Synthesis, Reactivity, Structure and Uses," *Coordination Chemistry Reviews*, vol. 112, (1992), pp. 47–79.

Chen et al., "Iodofluoroalkylsulfonyl Fluorides Synthesis and Conversion to New Derivatives," *J. Fluorine Chemistry*, vol. 43 (1989) pp. 329–347.

Waterfeld, "A New Cyclic Fluorinated Trisulfone $(CF_2SO_2)_3$ and Fluorinated Derivatives: $SO_2(CF_2SO_2F)_2$, $CF_2(SO_2CF_3)_2$, $CF_3SO_2CF_2SO_2F$, $CF_2(SO_2F)_2$ andCF$_3$SO$_2$CF$_2$SO$_2$CF$_2$SO$_2$F," *J. Fluorine Chemistry*, vol. 67 (1994) pp. 27–31.

Terjeson et al., "New Fluorosulfonyl–Containing Monomers/Polymers," *J. Fluorine Chemistry*, vol. 38 (1988) pp. 3–18.

Gard et al., "(Pentafluoro–$\lambda^6$–sulfanyl)difluoromethanesulfonyl Fluoride and Derivatives," *Inorg. Chem.* vol. 29 (1990) pp. 4588–4590.

Singh et al., "Chemistry of Perfluoromethylsulfonyl Perfluorobutylulfonyl Imide," *Inorg. Chem.*, vol. 29, (1990) pp. 2982–2984.

Stang et al., "Perfluoroalkanesulfonic Esters: Methods of Preparation and Applications in Organic Chemistry," *Synthesis*, (1982) pp. 85–124.

Des Marteau, *Novel Fluorinated Acids For Phosphoric Acid Fuel Cells*, Gas Res. Inst. Rep. #PB93–132710, (Jul. 1992).

Temple, Stanley, "The Reaction of Sulfuryl Fluoride and Sulfonyl Florides with Fluoro Olefins," *J. Organic Chemistry*, vol. 33 No. 1, (1968) pp. 344–346.

Banks, R. E., (ed )*Preparation, Properties, and Industrial Applications of Organofluorine Compounds*, ed. John Wiley: New York, (1982) pp. 37–43.

(List continued on next page.)

*Primary Examiner*—Peter O'Sullivan
*Attorney, Agent, or Firm*—Douglas B. Little; Daniel C. Schulte

[57] ABSTRACT

A method for preparing fluoroalkylsulfonyl imides by reacting a fluoroalkylsulfonamide with a fluoroalkylsulfonyl halide or a fluorosulfonyl halide in the presence of a non-nucleophilic base. One reaction is:

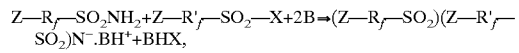

where each Z is a fluorine atom or a polymerizable organic functional group, $R_f$ and $R'_f$ are fluoroalkylene groups optionally containing catenary oxygen or nitrogen, X is a halogen atom, and B is a non-nucleophilic base.

Unsymmetrical imides and polymeric imides can be prepared.

8 Claims, No Drawings

OTHER PUBLICATIONS

Haszeldine et al., "Perfluoroalkylk Derivatives of Sulphur. Part II," *J. Chem. Soc.*, (1955) pp. 2901–2010.

D.D. Desmarteau, et al., "N–Fluoro–bis(trifluoromethane-sulphonyl)imide. An Improved Synthesis," Journal of Fluorine Chemistry, vol. 52, No. 1, pp. 7–12, (1991).

I.P. Bleeker, et al., "1H and 13C CIDNP Study of the Radical Rearrangement Involved in the Reaction of tert–Butylsulfinyl Chloride with N–Hydroxysulfonamides," vol. 46, No. 5, pp 1012–1014, (1981).

PREPARATION OF BIS (FLUOROALKYLENESULFONYL) IMIDES AND (FLUOROALKYSULFONY) (FLUOROSULFONYL) IMIDES

This application is a continuation-in-part of application Ser. No. 08/398,859 filed Mar. 6, 1995, now U.S. Pat. No. 5,514,493.

TECHNICAL FIELD

This invention relates to a method for preparing bis(fluoroalkylsulfonyl)imides, (fluoroalkylsulfonyl)(fluorosulfonyl)imides and derivatives thereof.

BACKGROUND

Bis(Fluoroalkylsulfonyl)imides, (fluoroalkylsulfonyl)(fluorosulfonyl)imides and derivatives thereof are known to be useful in many chemical processes and formulations. In solution, the imides behave as strong acids due to the presence of the electron-withdrawing fluoroalkylsulfonyl or fluorosulfonyl groups and exhibit exceptional stability under a variety of conditions. These compounds have been found to be useful, for example, as fuel cell electrolytes, as esterification catalysts and as polymerization catalysts for cationically-sensitive monomers such as epoxy resins.

The salts of bis(fluoroalkylsulfonyl)imides and (fluoroalkylsulfonyl)(fluorosulfonyl)imides have been found useful as electrolytes in advanced high voltage batteries. In particular, lithium bis(trifluoromethylsulfonyl) imide $(CF_3SO_2)_2N^-Li^+$, shows excellent conductivity and stability, but can be corrosive toward aluminum. Certain higher homologues of this compound show comparable performance as battery electrolytes, and have decreased the corrosion toward aluminum.

There are several known methods for preparing some classes of bis(fluoroalkylsulfonyl)imides. Bis(perfluoroalkylsulfonyl)imides can be prepared by the reaction of an alkali metal salt of an N-trimethylsilyl perfluoroalkylsulfonamide with a perfluoroalkylsulfonyl fluoride in a polar organic solvent. This route requires several synthetic steps, with the isolation of intermediate compounds, and the overall yields are often low. A second method involves the reaction of an alkali metal salts of a perfluoroalkylsulfonamide with perfluoroalkylsulfonyl fluoride in a polar organic solvent. Here too, the yields are low. A third method involves reacting a perfluorinated sulfonic anhydride with urea and a sulfonic acid. The products of this reaction are then dissolved in water and the addition of tetrabutylammonium bromide precipitates the tetrabutylammonium imide. This method is not satisfactory for the large scale production of imides because the overall yields are low and the sulfonic anhydride precursors are not easily accessible. A fourth method of making metal salts of sulfonimides involves the reaction of a metal nitride with perfluoroalkyl sulfonyl halide. However this method cannot be used to make unsymmetrical imides and requires handling metal nitrides which are sensitive to air.

Thus there remains a need for an efficient method of preparing bis(fluoroalkylsulfonyl)imides, (fluoroalkylsulfonyl)(fluorosulfonyl)imides, and derivatives thereof.

DISCLOSURE OF THE INVENTION

The present invention provides an efficient, high yield method of preparing bis(fluoroalkylsulfonyl)imides, (fluoroalkylsulfonyl)(fluorosulfonyl)imides as well as derivatives such as the organic or inorganic salts, and N-halo, N-alkyl or N-silyl compounds; hereinafter described as "imides" for the sake of brevity. The method uses readily available starting materials and allows the preparation of the imides in a single step, without the isolation and purification of intermediate compounds. The method of this invention also features the preparation of unsymmetrical imides and polymers having imide groups in the polymer chain.

By this method, a fluoroalkylsulfonamide is contacted with a fluoroalkylsulfonyl halide or a fluorosulfonyl halide, in the presence of a sufficient amount of a non-nucleophilic base at a temperature and for a time sufficient to yield the imide salt. Preferably, the fluoroalkylsulfonamide is prepared in situ by contacting a fluoroalkylsulfonyl halide with anhydrous ammonia.

DETAILED DESCRIPTION

In one aspect, the method of the invention may be represented by the following Scheme 1:

Scheme 1

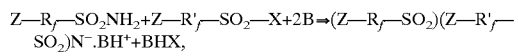

$Z-R_f-SO_2NH_2+Z-R'_f-SO_2-X+2B \rightarrow (Z-R_f-SO_2)(Z-R'_f-SO_2)N^-.BH^+ +BHX$, wherein $R_f$ and $R_f'$ are fluoroalkylene groups having from 1 to 12 carbon atoms, optionally containing one or more catenary oxygen or nitrogen atoms, each Z is a fluorine atom or a polymerizable organic functional group, X is a halogen atom and B is a non-nucleophilic base. $BH^+$ represents an cation derived from the non-nucleophilic base B, e.g. an ammonium cation, but other cations may be used. In the case of symmetrical imides, the sulfonamide is preferably generated in situ by the reaction of a sulfonyl halide with anhydrous ammonia. The sulfonamide then reacts with another molecule of sulfonyl halide to produce the bis(fluoroalkylenesulfonyl)imide as shown in Scheme 2:

Scheme 2

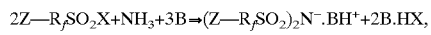

$2Z-R_fSO_2X+NH_3+3B \rightarrow (Z-R_fSO_2)_2N^-.BH^+ + 2B.HX$,

When sulfonamides are used as the starting compounds in the preparation of bis(fluoroalkylenesulfonyl)imides according the method of this invention, either the sulfonamide per se, or a salt of the sulfonamide may be used. As used herein, the term "sulfonamide" represents both the sulfonamides and the salts thereof. Thus, the use of fluoroalkylenesulfonamide salts may be represented in Scheme 3.

Scheme 3

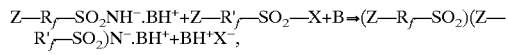

$Z-R_f-SO_2NH^-.BH^+ + Z-R'_f-SO_2-X+B \rightarrow (Z-R_f-SO_2)(Z-R'_f-SO_2)N^-.BH^+ +BH^+X^-$, In another aspect of the invention, polymeric bis(fluoroalkylenesulfonyl)imides may be prepared by contacting equimolar amounts of difunctional fluoroalkylene sulfonyl halides and fluoroalkylene sulfonamides in the presence of a non-nucleophilic base. The difunctional sulfonyl halides or sulfonamides may be fluoroalkylene disulfonyl halides or fluoroalkylene disulfonamides. Alternatively, a difunctional sulfonamidofluoroalkylenesulfonyl halide may be used. The preparation of polymeric imides is shown in Schemes 4–6.

Scheme 4

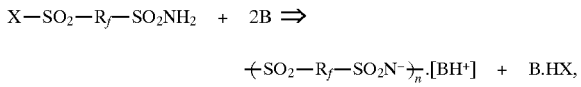

where n is an integer greater than 1, and X is preferably a fluorine atom.

Scheme 5

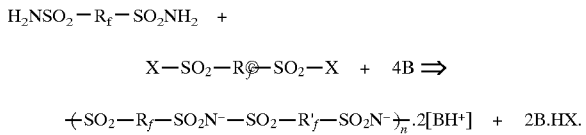

Scheme 6

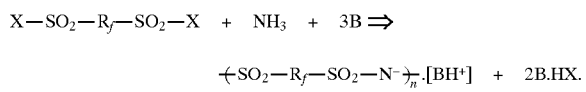

In Scheme 6, the sulfonamide is generated in situ by the reaction between a sulfonyl halide and ammonia in the presence of a non-nucleophilic base B. The sulfonamide thus produced reacts with a sulfonyl halide from another molecule of X—SO₂—R$_f$—SO₂—X to produce the imide. Where sulfonamides are used as starting compounds, either the sulfonamide per se can be used, or a salt as previously described. Preferably X—SO₂—R$_f$—SO₂—X is chosen so that the R$_f$ group is sufficiently large to make intramolecular cyclization unfavorable. Cyclization would be unfavorable when the resulting cyclic compound would have a ring size $\leq$ four ring atoms or $\geq$ nine ring atoms.

In the preparation of polymeric imides according to Schemes 4–6 it is preferable that the reagents be of the highest possible purity (e.g., >99% by weight) and have a high level of difunctionality (e.g., >99%) so that the reaction proceeds to high levels of conversion (e.g., >98%) with minimal side reactions in order to maximize the molecular weight of the final polymer.

(Fluoroalkylsulfonyl)(fluorosulfonyl)imides can be prepared by the method of this invention using a 5 fluoroalkyl-sulfonamide and a fluorosulfonyl halide according to Scheme 7.

Scheme 7

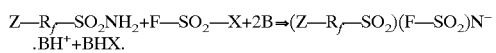

The fluoroalkylsulfonamide is preferably generated in situ by the reaction between a fluoroalkylsulfonyl halide and ammonia, and subsequently reacted with the fluorosulfonyl halide to produce the imides. As previously described, the fluoroalkylsulfonamide per se may be used, or a salt as shown in Scheme 8.

Scheme 8

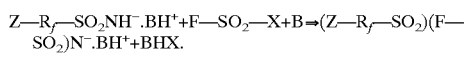

Difunctional fluoroalkylenesulfonamides may also be reacted with monofunctional fluoroalkylenesulfonyl halides, or conversely, difunctional fluoroalkylenesulfonyl halides may be reacted with monofunctional fluoroalkylenesulfonamides to produce dimeric bis(fluoroalkylenesulfonyl) imides, as shown in Schemes 9 and 10.

Scheme 9

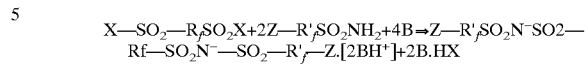

Scheme 10

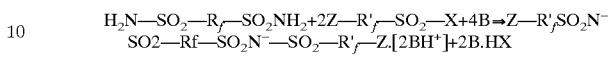

The fluoroalkylene groups, R$_f$ and R$_f'$, of the fluoroalkylenesulfonyl halides and the fluoroalkylenesulfonamides may be linear, branched, cyclic or acyclic, or combinations thereof. Additionally one or more of the fluorine or hydrogen atoms of the fluoroalkylene group may be replaced by chlorine or bromine atoms. In the above formulae shown in Schemes 1 to 10, one or more non-adjacent carbon atoms of the fluoroalkylene groups R$_f$ and R$_f'$ may be replaced by catenary divalent oxygen or trivalent nitrogen atoms.

When the fluoroalkylene group is acyclic it has the general formula $C_mH_{(2m-a)}F_a$, where m is 1 to 12 and a is at least one. When the fluoroalkylene group contains a cyclic group it has the general formula $C_mH_{(2m-2-a)}F_a$, where m is 1 to 12 and a is at least one. Preferably the sum of carbon atoms in the two fluoroalkylene groups of the bis (fluoroalkylenesulfonyl)imide is 3 to 12 carbon atoms Preferably, the fluoroalkylene group is substantially fluorinated so that the number of fluorine atoms is greater than the number of hydrogen atoms present. Most preferably the fluoroalkylene group is a linear or branched, cyclic or acyclic perfluoroalkylene group containing 1 to 10 carbon atoms and the sum of carbon atoms, in the two fluoroalkylene groups of the bis(fluoroalkylenesulfonyl)imide is 3 to 12 carbon atoms.

The halide X may be F, Br or I, but is preferably F. When Z is a polymerizable organic functional group it allows the preparation of polymers having pendant bis (fluoroalkylenesulfonyl)imide moieties on the polymer chain. Fluoroalkylenesulfonylfluorides having polymerizable functional groups have been described by Gard et al., J. Fluorine Chem. 66, 105(1994), Gard et al., Coordination Chemistry Reviews 112, 47(1992), Gard et al., J. Fluorine Chem. 49, 331(1990), Gard et al. J. Fluorine Chem. 43, 329(1989), Gard et al., J. Fluorine Chem. 67, 27(1994), Gard et al. J. Fluorine Chem. 55, 313(1991), Gard et al. J. Fluorine Chem. 38, 3(1988), Gard et al., Inorg. Chem., 29, 4588 (1990) U.S. Pat. No. 5,414,117 (Armand) and U.S. Pat. No. 5,463,005 (Desmarteau). Polymers prepared from fluoro-alkylenesulfonylfluorides having polymerizable functional groups have been described in DesMarteau, *Novel Fluorinated Acids for Phosphoric Acid Fuel Cells*, Gas Research Institute Report #GRI-92/0385, July 1992, and J. Fluorine Chem. 72,203 (1995).

Z may be any organic functional group that may undergo grafting or polymerization by an addition or step-growth mechanism, including cationic, anionic, free-radical and Z-N polymerization or polycondensation. Z may be chosen from those groups containing double bonds, for example vinyl, allyl, vinyl-benzyl or acryloyl groups. Z may also be chosen from those groups containing oxirane, oxetane, azetidine, or aziridine functional groups. Z may also be chosen from those groups containing alcohol, amine, isocyanate, or trialkoxysilyl functional groups.

When Z contains functional groups whose reactivity could interfere with reactions for preparing the imides, Z can be protected by reactants that are reversibly bound to it. For example, a double bond may be protected as a di-halo derivative and subsequently dehalogenated. Examples of Z include $CH_2=CH-$, $CH_2=CHO-$, $CH_2=CHCH_2O-$, $CH_2=CHCO_2-$, $(CH_2=CHCH_2)_2NCO-$ (prepared as described in Armand et.al, U.S. Pat. No. 5,414,117), $(CH_2=CHCH_2)_2NSO_2-$ $CF_2=CFO-$, $CF_2=CF-$, $CH_2=CHCO_2CH_2CH_2-$, $-O-$ $C_6H_4-CH=CH_2$, $-C(O)OCH_2CH_2OC(O)C(CH_3)=CH_2$, $-C(O)NCH_2CH_2OC(O)C(CH_3)=CH_2$, $-SO_2O-C_6H_4-CH=CH_2$, $-OCH_2CHOH-CH_2OH$, $-C(O)C(CH_3)=CH_2$, $-C(O)OCH_2CH=CH_2$, and $-OCH_2C\equiv CH$.

Perfluoroalkylsulfonyl fluorides and perfluoroalkylenedisulfonyl fluorides used as precursors to the imide salts of this invention can be prepared by a variety of methods known in the art as described, for example, in U.S. Pat. Nos. 3,542,864; 5,318,674; 3,423,299; 3,476,753, 3,776,960, 2,519,983, 3,951,762; 3,623,963; 2,732,398 S. Temple, *J.Org. Chem.*, 33(1), 344 (1968), D. D. DesMarteau, *Inorg. Chem.*, 32, 5007 (1993), and *Chemistry of Organic Fluorine Compounds*, M. Hudlicky, ed., 2nd ed. PTR Prentice Hall (New York), pp. 73–6, all of which are incorporated herein by reference.

Perfluoroalkylsulfonyl fluorides are available by the electrochemical fluorination of the corresponding alkylsulfonyl fluorides as described in U.S. Pat No. 2,732,398 (Brice et al.), the description of which is incorporated herein by reference. See also T. Abe et al., in *Preparation, Properties and Industrial Applications of Organofluorine Compounds*, R. E. Banks(Ed), pages 37–9, John Wiley & Sons, New York (1982). Routes to perfluoroalkanesulfonyl chlorides are described by P. J. Stag et al. in Synthesis 1982, 85 and by R. N. Haszeldine et al., in J. Chem. Soc. 1955, 2901. The chlorides of ω-hydrofluorinated sulfonic acids are described by Coffman and Raasch in J. Org. Chem,. 14, 747 (1949), by Weiyuan et al. in Chemistry 2, 31 (1987), and by Huang, J. Fluorine Chem. 32, 179 (1986).

Ammonia, when used in the method of this invention, should be anhydrous to prevent side reactions from occurring. To avoid the hazards of handling liquid ammonia, it is often convenient to generated anhydrous ammonia in situ by reacting ammonium salts of the formula $NH_4^+X^-$ with one equivalent of a non-nucleophilic base. Here X may be any halide, or any other non-reactive anion.

For purposes of this description, the term "non-nucleophilic base" B means a base which does not undergo an irreversible reaction with the sulfonyl halide group. This reaction, when it occurs will reduce the yields of the desired imide. The non-nucleophilic base may be an organic or inorganic base, but is preferably an organic aprotic base. Examples of suitable organic non-nucleophilic bases include alkylamines, for example triethyl amine, trimethyl amine, tripropyl amine and diisopropylethyl amine, pyridines, alkyl pyridines and dialkylaminopyridines, alkyl piperadines, dialkyl piperazines, N-alkyl pyrrolidines, N-alkylpyrroles N-alkylimidazoles, amidines, for example 1,5-diazabicyclo[4.3.0]non-5-ene (DBN) or 1,8-diazabicyclo[5.4.0]dec-7-ene (DBU), or guanidines.

It is preferable to prepare the bis(fluoroalkylenesulfonyl) imides neat, i.e. in the absence of any solvent. Generally a solvent is not necessary, the reactants are sufficiently soluble in each other to produce the imides. In some cases, solvents may be added to enhance the solubility of the reactants, such as when preparing polymeric imides from difunctional sulfonyl halides and/or sulfonamides. Any solvent that is non-reactive toward the starting sulfonyl halides and sulfonamides may be used, but polar aprotic solvents are preferred. Any solvent used should be anhydrous, (e.g., less than 1% water) to avoid competing hydrolysis of the sulfonyl halides. Examples of suitable aprotic liquids include linear ethers such as diethyl ether, diethylene glycol dimethyl ether, and 1,2-dimethoxyethane; cyclic ethers such as tetrahydrofuran, 2-methyltetrahydrofuran, dioxane, dioxolane, and 4-methyldioxolane; nitriles such as acetonitrile and benzonitrile; nitro compounds such as nitromethane or nitrobenzene; amides such as N,N-dimethylformamide, N,N-diethylformamide, and N-methylpyrrolidinone; sulfoxides such as dimethyl sulfoxide; sulfones such as dimethylsulfone, tetramethylene sulfone, and other sulfolanes; oxazolidinones such as N-methyl-2-oxazolidinone and mixtures thereof.

The method of this invention can be carried out by introducing the reactants into a vessel, which can be made of glass or other corrosion-resistant material. Preferably the vessel is suitable for use at elevated pressures caused by the high vapor pressure(s) of certain reagents (e.g., $NH_3$). The method of this invention can generally by carried out by heating the contents of the vessel at temperatures from about $-25°$ C. to about $150°$ C., preferably from $25°$ C. to about $100°$ C. and at a pressure equal to or greater than atmospheric. Generally pressures in excess of those generated by the vapor pressures of the reagents at the reaction temperatures is not required.

When preparing non-polymeric imides from fluoroalkyl-sulfonamides generally at least one molar equivalent of the sulfonyl halide is used. Preferably a slight stoichiometric excess of the sulfonyl halide is used. When preparing imides from ammonia, as shown in Scheme 2, a stoichiometric excess of sulfonyl halide, relative to the amount of ammonia, is generally preferred. The amount of non-nucleophilic base used is generally in excess of the stoichiometric amount shown in Schemes 1 through 6. Preferably the amount of base is less than a 100% excess of the stoichiometric amount shown in the Schemes. Most preferably amount of base is less than a 50% excess of the stoichiometric amount shown in the Schemes to maximize the volume efficiency of the reaction.

Representative imides that can be prepared by the method of this invention include:

$^-N(SO_2CF_3)_2$    $^-N(SO_2C_2F_5)_2$    $^-N(SO_2C_4F_9)_2$
$^-N(SO_2C_8F_{17})_2$    $^-N(SO_2CF_2CF_2CFClCF_2Cl)_2$
$^-N(SO_2CF_2\text{-c-}C_6F_{11})_2$    $^-N(SO_2CF_2CF_2OCFClCF_2Cl)_2$
$^-N(SO_2C_3F_6CF_2Cl)_2$    $^-N(SO_2C_3F_6CF_2H)_2$    $^-N(SO_2C_2F_4N(CF_3)_2)_2$
$^-N(SO_2CF_2CF_2OCF=CF_2)_2$    $^-N(SO_2CF_2CF_2OCF_3)_2$    $^-N(SO_2CF_2CF_2CF=CF_2)_2$
$^-N(SO_2C_4F_8OCH=CH_2)_2$    $^-N(SO_2C_2F_4OCH_2CH=CH_2)_2$    $^-N(SO_2CF_3)(SO_2C_2F_5)$
$^-N(SO_2CF_3)(SO_2C_4F_9)$    $^-N(SO_2CF_3)(SO_2C_8F_{17})$    $^-N(SO_2C_2F_5)(SO_2C_4F_9)$
$^-N(SO_2CF_3)(SO_2F)$    $^-N(SO_2C_4F_9)(SO_2F)$    $^-N(SO_2CF_3)(SO_2CF_2H)$
$^-N(SO_2CF_3)(SO_2C_2F_4N(CF_3)_2)_2$    $^-N(SO_2CF_3)(SO_2C_2F_4CFClCF_2Cl)$
$^-N(SO_2CF_3)(SO2C2F4OCFClCF2Cl)$    $^-(SO_2CF_3)(SO_2C_2F_4OCF=CF_2)$
$^-N(SO_2CF_3)(SO_2C_2F_4OCF_3)$    $^-N(SO_2CF_3)(SO_2C_2F_4CF=CF_2)$ -continued ⁻N(SO₂CF₃) (SO₂C₂F₄OCH₂CH=CH₂)
⁻N(SO₂CF₃) (SO₂C₂F₄OC₃F₆OCF=CF₂)
⁻N(SO₂CF₃) (SO₂C₂F₄OC₂F₄CH=CH₂)
⁻N(SO₂CF₃) (SO₂C₂F₄OCH₂CHOHCH₂OH)
⁻N(SO₂CF₃) (SO₂CF₂C(O)OCH₂CH=CH₂)

⁻N(SO₂CF₃) (SO₂C₃F₆CF₂H)
⁻N(SO₂CF₃) (SO₂C₄F₈OCH=CH₂)
⁻N(SO₂CF₃) (SO₂C₂F₄CON(CH₂CH=CH₂)₂)
⁻N(SO₂CF₃) (SO₂C₂F₄COC(CH₃)=CH₂)
⁻N(SO₂CF₃) (SO₂C₂F₄OCH₂C≡CH)

CF₃SO₂N⁻SO₂C₄F₈SO₂N⁻SO₂CF₃
⁻N(SO₂C₂F₄OC₂F₄CH=CH₂)₂

C₂F₅SO₂N⁻SO₂(CF₂)₆SO₂N⁻SO₂C₂F₅
⁻N(SO₂CF₂C(O)N(CH₂CH=CH₂)₂)₂

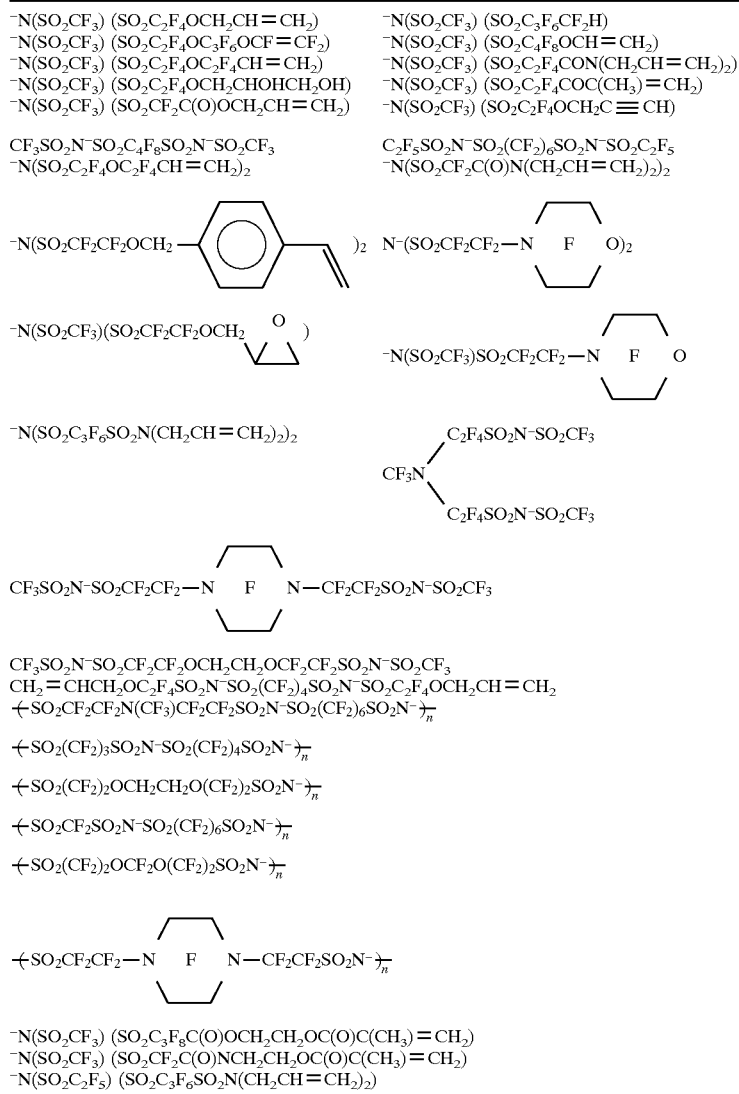

⁻N(SO₂C₃F₆SO₂N(CH₂CH=CH₂)₂)₂

CF₃SO₂N⁻SO₂CF₂CF₂OCH₂CH₂OCF₂CF₂SO₂N⁻SO₂CF₃
CH₂=CHCH₂OC₂F₄SO₂N⁻SO₂(CF₂)₄SO₂N⁻SO₂C₂F₄OCH₂CH=CH₂
‒(SO₂CF₂CF₂N(CF₃)CF₂CF₂SO₂N⁻SO₂(CF₂)₆SO₂N⁻)ₙ‒

‒(SO₂(CF₂)₃SO₂N⁻SO₂(CF₂)₄SO₂N⁻)ₙ‒

‒(SO₂(CF₂)₂OCH₂CH₂O(CF₂)₂SO₂N⁻)ₙ‒

‒(SO₂CF₂SO₂N⁻SO₂(CF₂)₆SO₂N⁻)ₙ‒

‒(SO₂(CF₂)₂OCF₂O(CF₂)₂SO₂N⁻)ₙ‒

⁻N(SO₂CF₃) (SO₂C₃F₈C(O)OCH₂CH₂OC(O)C(CH₃)=CH₂)
⁻N(SO₂CF₃) (SO₂CF₂C(O)NCH₂CH₂OC(O)C(CH₃)=CH₂)
⁻N(SO₂C₂F₅) (SO₂C₃F₆SO₂N(CH₂CH=CH₂)₂)

The imides shown (without a corresponding cation for illustrative purposes) can be used to prepare derivatives such as alkali, alkaline earth and other metal salts, N-silyl imides, N-alkyl and N-fluoro imides. For example, conjugate acids of the imides may be treated with an inorganic base having the desired cation $M^+$, such as NaOH, LiOH, KOH, NH₄OH, Ag₂CO₃ or CuO, to produce the corresponding N—Na, N—Li, N—K, N—NH₄, N—Ag or N—Cu salts. The imides may be contacted with fluorine under direct fluorination conditions to produce the N—F derivatives. The silver imide salts may be contacted with a trialkylsilyl chloride, trialkylstannyl chloride, or an alkyl halide to produce the N-trialkylsilyl, N-trialkylstannyl or N-alkyl derivatives respectively. Other derivatives can be prepared by means known to those skilled in the art.

The invention is further illustrated by the following Examples. In the examples, the term "reduced pressure" means the vacuum obtained by means of a commercially available laboratory distillation apparatus using an aspirator connected to a water pipe or other fluid stream for aspiration, such as a rotary evaporator apparatus.

EXAMPLE 1

Lithium(trifluoromethanesulfonyl) (perfluorobutanesulfonyl)imide

Under a nitrogen atmosphere, a dry, 500 mL Fisher-Porter pressure bottle equipped with a stainless steel pressure head and magnetic stirrer was charged with 35.00 g $CF_3SO_2NH_2$ (prepared, e.g., as described in Foropoulos and DesMarteau, Inorg. Chem., 23:3720–23 (1984)), 98 mL anhydrous triethylamine and 74.55 g $C_4F_9SO_2F$. The pressure vessel was sealed and the reaction mixture heated to 90° C. with stirring for 17 hours. The volatile components of the reaction mixture were evaporated under reduced pressure at 70° C. then the reaction mixture was treated with a mixture of 700 mL water and 700 mL methylene chloride with stirring to form a two phase mixture. The methylene chloride phase was then separated, washed with two 700 mL portions of water, dried over anhydrous $MgSO_4$, filtered and then evaporated under reduced pressure to yield a dark red liquid. This liquid was combined with 500 g of polyphosphoric acid (Aldrich Chemical Co.) in a short path vacuum distillation apparatus equipped with an ambient air-cooled condenser, and then vacuum distilled at ca. 0.1 Torr. The distillate (96.5 g, corresponding to $HN(SO_2CF_3)(SO_2C_4F_9)$, which solidified in receiver at 0° C., was further purified by sublimation at 70° C., 1.0 Torr and then added in portions to a slurry of 52 g of $Li_2CO_3$ (99.997% purity, from Aldrich Chemical Co.) in 800 mL of methyl t-butyl ether with stirring at room temperature. After about 1 hour $CO_2$ evolution subsided and the reaction mixture was heated to about 40° C. for 3.5 hours to complete the neutralization. The mixture was filtered by gravity through filter paper and then filtered again by suction through a 0.22 micron Tefsep® Teflon membrane (Micron Separations Inc., Westboro, Mass.) to remove particulates. The filtrate was evaporated under reduced pressure at 25°–80° C. to yield a clear, colorless oil. Two 250 mL portions of toluene were combined with the oil and the mixture evaporated at 40°–70° C., 20 Torr after each toluene addition, causing the oil to eventually solidify giving a fine white powder. The solid was transferred to a glass jar and dried in vacuo at 100° C., $10^{-2}$ Torr for 24 hours to yield 77.0 g of the anhydrous title salt. The structure of the product was confirmed by $^1H$ and $^{19}F$ NMR spectroscopy which indicated that the purity of the salt was greater than 99% by weight.

EXAMPLE 2

Lithium (trifluoromethanesulfonyl) (perfluoroethanesulfonyl)imide

Under a nitrogen atmosphere, a dry 3 L flask equipped with a dry ice condenser, mechanical stirrer, and a sparging tube was charged with 500 mL anhydrous methyl t-butyl ether (MTBE) and cooled below 0° C. in a dry ice bath. To the cold solvent was added 500 g of crude $CF_3CF_2SO_2F$ mixture (containing ca. 23% $CF_3CF_2SO_2F$ by weight in C6–C8 perfluoroalkane solvent). Gaseous anhydrous ammonia (194 g) was gradually introduced through the sparging tube into the resulting mixture at ca. 0° C. with vigorous stirring. Once ammonia addition was complete, the reaction was allowed to proceed for an additional hour after which the dry ice bath was removed and the reaction solution gradually warmed to room temperature with stirring. Excess ammonia was allowed to evaporate while stirring overnight at room temperature. The reaction solution was cooled again to 0° C. and treated with 83.9 g $LiOH.H_2O$ dissolved in 750 mL of water with stirring. The mixture was filtered through filter paper by gravity to remove LiF precipitate. To the filtrate was added concentrated aqueous HCl in portions with stirring at 0° C. until the pH of the mixture was 0.

The resulting two-phase mixture was separated into separate aqueous and ether phases. The aqueous phase was extracted with two additional 400 mL portions of MTBE. The ether fractions were combined, extracted with two 500 mL portions of water, and then dried over anhydrous $MgSO_4$ overnight. The ether solution was filtered by gravity through filter paper and then by suction through a 0.22 micron Tefsep™ membrane (Micron Separations Inc.). The filtrate was concentrated by rotary evaporation, hexane was added, and the solution concentrated again. This was repeated until the product $CF_3CF_2SO_2NH_2$ crystallized from solution as a white solid. The product (Crop 1) was isolated by suction filtration through a glass frit giving 33.0 g. A second crop of crystals (20.2 g) was recovered in the same manner from the filtrate by concentrating further followed by filtration. The remaining filtrate was evaporated to dryness at 40° C., 20 torr to yield a third crop of relatively crude product (26.8 g). All product fractions (Crops 1–3) were dried at $10^{-2}$ torr at room temperature for ca. 15 min to give a combined yield of 80.0 g. Quantitative $^1H$ and $^{13}C$ NMR analysis of the product from Crop 2 indicated that it was the desired product with a purity of 98% by weight.

Under a nitrogen atmosphere, a dry Parr 4560-Series Benchtop Mini Reactor equipped with a 600 mL capacity Monel reactor cylinder, mechanical stirrer, thermocouple and heating mantle was charged with 53 g $CF_3CF_2SO_2NH_2$ (Crops 1+2) and 152 mL anhydrous triethylamine. While cooling the reactor at −78° C. in dry ice, 55.2 g of gaseous $CF_3SO_2F$ (ca. 94% purity) was condensed into the reactor with stirring. The reactor was sealed and the temperature of the reaction mixture gradually raised to 90° C. with vigorous stirring, then held at 90° C. with stirring for a total of 24 hours. The volatile components of the reaction mixture were evaporated under reduced pressure at 70° C., then the residue was treated with a mixture of 700 mL water and 700 mL methylene chloride with stirring to form a two phase mixture. The methylene chloride phase was then separated, washed with two 700 mL portions of water, dried over anhydrous $MgSO_4$, filtered and then evaporated under reduced pressure to yield a dark red liquid. This liquid was combined with 600 g of polyphosphoric acid (Aldrich Chemical Co.) in a short path vacuum distillation apparatus equipped with an ambient air-cooled condenser, and then vacuum distilled at ca. 15 torr, 85°–88° C. The distillate (78.1 g, corresponding to $HN(SO_2CF_3)(SO_2C_2F_5)$ ), which solidified in receiver at 0° C., was converted to the corresponding lithium salt, and further purified, using essentially the procedure described in Example 1 to yield 75.0 g of the anhydrous title salt. The structure of the product was confirmed by $^1H$ and $^{19}F$ NMR spectroscopy which indicated that the purity of the salt was 98% by weight.

EXAMPLE 3

Lithium Bis(perfluoroethanesulfonyl)imide

As in Example 2, a dry Parr 4560-Series Benchtop Mini Reactor was charged with 155 mL anhydrous triethylamine. While cooling the reactor at −78° C. in dry ice, gaseous $C_2F_5SO_2F$ (100.0 g, >99% purity) followed by anhydrous ammonia (3.51 g) were condensed into the reactor with stirring. The reactor was sealed and the temperature of the reaction mixture gradually raised to 90° C. with vigorous stirring. The reaction mixture was held at 90° C. with stirring for a total of 20.5 hours. The intermediate product, $HN(SO_2C_2F_5)_2$, was isolated as previously described, then added to a slurry of $Li_2CO_3$ (45.7 g, 99.997% purity) in 800 mL of methyl t-butyl ether to produce the lithium salt. This lithium salt was isolated using essentially the procedure described in Example 1 to yield 73.34 g (92% yield based upon $NH_3$) of the anhydrous title salt. The structure of the product was confirmed by $^1H$ and $^{19}F$ NMR spectroscopy which indicated that the purity of the salt was 99.9% by weight.

EXAMPLE 4

Lithium Bis(perfluorobutanesulfonyl)imide

As in Example 1, a dry, 500 mL Fisher-Porter pressure bottle was charged with anhydrous triethylamine (100.5 g) and $C_4F_9SO_2F$ (145.0 g). The pressure vessel was sealed, cooled to −78° C. in dry ice and then charged with of anhydrous ammonia (3.0 g) with stirring. After warming gradually to room temperature, the reaction mixture was heated to 90° C. with stirring 24 hours. The intermediate product, $HN(SO_2C_4F_9)_2$, was isolated as previously described, then added to a slurry of $Li_2CO_3$ (40.0 g, 99.997% purity) in 800 mL of methyl t-butyl ether to produce the lithium salt. This lithium salt was isolated using essentially the procedure described in Example 1 to yield 90.8 g (86% yield based upon $NH_3$) of the anhydrous title salt. The structure of the product was confirmed by $^1H$ and $^{19}F$ NMR spectroscopy which indicated that the purity of the salt was 98% by weight.

EXAMPLE 5

Lithium Bis(perfluoropropanesulfonyl)imide

As in Example 4, the title compound was prepared using anhydrous triethylamine (100.5 g), $C_3F_7SO_2F$ (100.0 g, 68:32 iso:normal isomer ratio), and anhydrous ammonia (3.0 g). A total of 40.8 g of the anhydrous title salt was recovered as a light pink solid. Quantitative analysis by $^1H$ and $^{19}F$ NMR spectroscopy indicated that the product contained the following major components in order of decreasing weight percent: $Li^{+-}N(SO_2C_3F_7)_2$, 85.1%, 39:61 iso:normal $C_3F_7$ ratio; $Li^{+-}N(SO_2i-C_3F_7)(SO_2F)$, 8.7%; $Li^{+-}N(SO_2n-C_3F_7)(SO_2F)$, 4.2%.

EXAMPLE 6

Synthesis of Lithium trifluoromethylsulfonyl perfluoro(dimethylaminoethylsulfonyl)imide $Li^{+-}N(SO_2CF_3)(SO_2C_2F_4N(CF_3)_2)$ The hydrocarbon precursor 2-dimethylaminoethylsulfonylfluoride was made by the addition of dimethylamine to vinylsulfonyl fluoride as described in Krutak et al., *J. Org. Chem.*, 44(2):3847–58 (1979). The hydrocarbon was perfluorinated by electrochemical fluorination. An electrochemical cell of the type described in U.S. Pat. No. 2,519,983 (Simons) was filled with 1500 cm$^3$ anhydrous HF. The cell was operated at 31 psig (214 Kpa) and at an average temperature of 56° C. During the course of the 129 hour run, 456 grams of fluorinated product was produced from 650 grams (4.2 mole) of starting material. Analysis of the fluorocarbons was done using gas chromatography/FTIR to confirm structures and yields. The resulting fluorochemical was distilled in a 3-plate distillation column to a main cut of 374 grams (1.1 moles, 27% molar yield) corresponding to perfluorodimethylaminoethylsulfonyl fluoride $((CF_3)_2NC_2F_4SO_2F)$.

To a dry flask equipped with a reflux condenser and magnetic stirrer was charged 1.13 g $CF_3SO_2NH_2$ (prepared, e.g., as described in Foropoulos and DesMarteau, *Inorg. Chem.*, 23:3720–23 (1984)), 20 mL anhydrous triethylamine (distilled from $LiAlH_4$) and 2.67 g $(CF_3)_2NC_2F_4SO_2F$. The reaction mixture was heated to 70° C. under a nitrogen atmosphere with stirring for 17 hours, after which volatile components were removed under reduced pressure. The residue was treated with a mixture of 40 mL water and 40 mL methylene chloride with stirring to form a two phase mixture. The methylene chloride phase was then separated, washed with two 40 mL portions of fresh water to remove water-soluble components, dried over anhydrous $MgSO_4$, filtered and then evaporated under reduced pressure to yield a dark red liquid. The liquid residue was combined with 20 mL of concentrated (at least 98 weight percent $H_2SO_4$) sulfuric acid in a short path distillation apparatus equipped with a dry-ice cooled condenser, and then vacuum distilled at $10^{-3}$ torr, 60° C. The distillate was dissolved in 50 mL of diethyl ether, after which the resulting ether solution was treated with excess lithium carbonate for 2 hours with stirring at room temperature, filtered and the filtrate evaporated under reduced pressure to yield a clear, colorless oil. Approximately 100 mL of toluene were combined with the oil and the mixture evaporated again at 40°–70° C., 20 torr, causing the oil to solidify to form the title salt. The structure of the product was confirmed by $^1H$ and $^{19}F$ NMR.

EXAMPLE 7

Preparation of Dilithio perfluoro(methyl-bis-trifluoromethylsulfonimidoethyl)amine $CF_3N(CF_2CF_2SO_2N^-SO_2CF_3)_2.2Li^+$ A 500 mL flask equipped with an addition funnel and stir bar was charged with 10 g of $CF_3SO_2NH_2$, 45 mL of dry THF and 45 mL of dry triethylamine, then cooled to 0° C. under nitrogen. 15 g of $CF_3N(CF_2CF_2SO_2F)_2$ (prepared by electrochemical fluorination of $CH_3N(CH_2CH_2SO_2F)_2$) was then added slowly to the stirred solution. After complete addition, the reaction was allowed to warm to room temperature and stirred for an additional 92 hours. Next, the mixture was evaporated to a brown oil under reduced pressure, which was then dissolved in 300 mL of aqueous 1M LiOH. The water, triethylamine and other volatile components were then evaporated under reduced pressure and the remaining solid washed with 100 mL of diethyl ether. The ether solution was filtered, then evaporated under reduced pressure to yield a brown oil, which was dissolved in a small amount (quantity just sufficient to dissolve the oil) of diethyl ether, then added to 100 mL of methylene chloride. This solution was again filtered and evaporated to yield 3.5 g of a yellow solid corresponding to the title salt. The structure was confirmed by $^1H$ and $^{19}F$ NMR.

EXAMPLE 8

Preparation of Lithium bis-perfluoro (dimethylaminoethyl)sulfonimide $Li^{+-}N(SO_2C_2F_4N(CF_3)_2)_2$ A 500 mL Fisher-Porter pressure bottle, equipped with a magnetic stir bar and pressure head, was charged with 30 g of $(CF_3)_2NC_2F_4SO_2NH_2$ (prepared by treatment of $(CF_3)_2NC_2F_4SO_2F$ (prepared by electrochemical fluorination of $(CH_3)_2NC_2H_4SO_2F)$) with excess ammonia in tetrahydrofuran), 27.4 g of triethylamine and 31.8 g of $(CF_3)_2NC_2F_4SO_2F$. The flask was sealed and heated to 100° C. for 37 hrs with stirring. After cooling, the volatile components of the reaction mixture were evaporated under reduced pressure. The residue was dissolved in 300 mL of methylene chloride and extracted three times with 300 mL of water each time. The methylene chloride solution was then dried over $MgSO_4$, filtered, and the solvent removed under reduced pressure. The residue was then distilled from excess polyphosphoric acid over a temperature and pressure range starting from 105° C. and 3 torr and ending at 97° C. and 0.2 torr to yield 40.13 g of a pale yellow-orange liquid which solidified on standing. This solid, corresponding to $HN(SO_2C_2F_4N(CF_3)_2)_2$, was dissolved in 300 mL of methyl t-butyl ether, after which 20.6 g of $Li_2CO_3$ was added in small portions with stirring. After stirring overnight, a small amount of additional $Li_2CO_3$ was added and heated briefly until the solution tested neutral to pH paper premoistened with distilled water. The mixture was cooled, filtered and the solvent removed under reduced pressure. Further drying under vacuum at 110° C. yielded 33.5 g of a fine white powder corresponding to the title salt. The structure of the product was confirmed by FTIR, and $^{19}F$ and $^1H$ NMR.

EXAMPLE 9

Synthesis of Lithium (trifluoromethylsulfonyl)(allyloxyoctaflurobutylsulfonyl)imide $(CH_2=CHCH_2OC_4F_8SO_2N(Li)SO_2CF_3)$ A 50 mL flask was charged with dry, distilled triethylamine (15 mL), dry acetonitrile (15 mL) and $CF_3SO_2NH_2$ (6.75 g, 0.0081 mole), purged with nitrogen, and cooled to about 0° C. in an ice bath. $CH_2=CHCH_2OC_4F_8SO_2F$ (3.0 g, 0.0082 mole, prepared essentially as described in Gard et al., J. Fluorine Chem,., 49, 331(1990) from $FC(O)(CF_2)_3 SO_2F$, which was prepared as described in U.S. Pat. No. 4,425,199) was added dropwise to the solution with stirring, and the reaction mixture was allowed to come to room temperature overnight.

The solvent from the resulting brown mixture was removed under reduced pressure, and aqueous LiOH (30 mL of 1M) was added. The mixture was stirred until neutralization was complete. The water was removed under reduced pressure and the resulting oil was dissolved in diethyl ether, then filtered to removed excess LiOH.

To the ether solution was added methylene chloride (25 mL) and sulfuric acid (15 mL of 2M). The organic layer was separated, neutralized with excess $Li_2CO_3$, filtered and the insoluble portion washed with acetonitrile. The volatile components of the combined filtrate solutions were removed under reduced pressure, and the resulting brown oil slowly crystallized to yield clear crystals of the title compound. The structure was confirmed by $^1H$ and $^{19}F$ NMR. Yield 2.73 g, 71%.

EXAMPLE 10

Preparation of Lithium (trifluoromethylsulfonyl) (fluorosulfonyl )imide, $CF_3SO_2NLiSO_2F$ A dry, 3-necked flask equipped with a nitrogen inlet, stir bar and dry-ice condensor was charged with dry triethylamine (15 mL)and cooled in a dry ice/isopropanol bath. Sulfuryl fluoride $SO_2F_2$ (7.0 g, 6.8 mmole) was bubbled into the cooled triethylamine. The reaction mixture was allowed to warm to −30° C., followed by dropwise addition of a solution of triethylamine(10 mL), acetonitrile (10 mL) and $CF_3SO_2NH_2$ (4.0 g, 0.027 mole). The temperature was maintained for an hour, allowed to warm to room temperature, and then stirred overnight.

The solvent was removed from the brown reaction mixture under reduced pressure. The remaining brown oil was dissolved in methylene chloride (75 mL) and washed with water, followed by 3M $H_2SO_4$, then dried over $MgSO_4$. The solvent was removed under reduced pressure, and the crude product purified by Kugelrohr distillation (80° C. at 1 torr) to yield $CF_3SO_2NHSO_2F$ as a clear oil. This imide was dissolved in methyl t-butyl ether, neutralized with excess $Li_2CO_3$, filtered and the solvent removed under reduced pressure to yield the title compound. Yield 3.5 g, 55%.

EXAMPLE 11

Preparation of Lithium (difluoromethylsulfonyl) (trifluoromethylsulfonyl)imide, $(HCF_2SO_2)(CF_3SO_2)NLi$ Difluoromethylsulfonyl chloride (30 g, 0.2 mole) was dissolved in diethyl ether (100 mL) and cooled to 0° C. An excess of anhydrous $NH_3$ was added until the conversion to the difluoromethylsulfonamide was complete by gas chromatography/mass spectroscopy. The ether solution was evaporated to yield a reddish oil, from which a yellow crystalline solid precipitated. The crystals were washed with diethyl ether, dried and then washed with hot toluene to remove yellow, oil impurities.

A mixture of the purified difluoromethylsulfonamide (26.5 g, 0.2 mole), triethylamine (60.6 g, 0.6 mole) and trifluoromethylsulfonyl fluoride (85% pure, 39.5 g, 0.26 mole)were charged into a stainless steel pressure vessel and heated at 45° C. for 24 hours. The lower phase was separated from the upper triethylamine phase, dissolved in methylene chloride, and washed with water. The solvent was removed under reduced pressure to yield $(HCF_2SO_2)(CF_3SO_2)N^- (Et)_3 NH^+$(38.9 g, 0.11 mole, 55%)

This ammonium salt was acidified with concentrated $H_2SO_4$ (20 g) and distilled at 100° C. and 5 torr to yield $(HCF_2SO_2)(CF_3SO_2)NH$ (9.8 g). This imide (15.3 g, 0.06 mole from two preparations) was treated with $LiOH.H_2O$ (2.5 g, 0.06 mole in 50 mL water). The solution was filtered and dried in a convection oven overnight at 100° C., Yield 14.1 g of $(HCF_2SO_2)(CF_2SO_2) N^-Li^+$.

EXAMPLE 12

Preparation of bis(trifluoromethylsulfonyl)imide

A stainless steel pressure vessel was charged with triethylamine (328 g, 3.25 mole), sealed, and cooled to 0° C. Trifluoromethylsulfonyl fluoride (103.4 g of 85% purity, 0.68 mole) was added to the vessel via a gas inlet, followed by anhydrous ammonia (4.76 g, 0.28 mole). The mixture was heated at 65° C. for 24 hours, cooled and the lower product phase decanted. The upper triethylamine phase was extracted with methylene chloride, then combined with the lower product phase and washed with water to remove by-product salts. The solvent was removed under reduced pressure to yield the crude salt: $(CF_3SO_2)N^-NH(C_2H_5)_3^+$. The salt was acidified with concentrated sulfuric acid (250 g), then purified by vacuum distillation to yield the title compound. Yield 64.6 g, b.p. 100° C. at 5 torr. This imide was dissolved in water (100 mL), then treated with $LiOH.H_2O$ (9.67 g, 0.23 mole). The solution was filtered, then dried to a white crystalline product in a convection oven at 100° C. Yield 64.9 g of lithium-bis-(trifluoromethylsulfonyl)imide. The structure was confirmed by $^{19}F$ NMR.

EXAMPLE 13

Preparation of $[(-SO_2(CF_2)_4SO_2N^-SO_2(CF_2)_3SO_2N^--) 2(C_2H_5)_3NH^+]_n$ Polymer The reagents $H_2NSO_2(CF_2)_4SO_2NH_2$ (1.995 g, 5.539 mmoles; prepared by electrochemical fluorination of $FSO_2(CH_2)_4SO_2F$ followed by amidation), $FSO_2(CF_2)_3SO_2F$ (1.751 g, 5.539 mmoles; prepared by electrochemical fluorination of $FSO_2(CH_2)_3SO_2F$), triethylamine (3.363 g, 33.23 mmoles. dried over activated 3A molecular sieves) and anhydrous acetonitrile (5 mL) were combined in a dry 2 oz (~59.1 mL) jar equipped with a magnetic stir bar and a tight-fitting cap to prevent significant exposure to ambient moisture. Once all reagents were fully dissolved, the contents were heated in an oil bath at 65° C. with stirring overnight. The temperature was then increased to 75° C. for 8 hours after which the reaction solution was allowed to cool to room temperature. Volatile components of the reaction mixture were removed under vacuum at 70° C. The remaining viscous residue was combined with a mixture of methylene chloride and water and agitated in a separatory funnel to extract by-product salts into the aqueous phase. The polymeric product was only partially soluble in the methylene chloride phase, the remainder separated out as a third viscous brown oil phase. The water fraction was separated and discarded, and the remaining two organic fractions were extracted an additional two times with water. The isolated organic fractions were concentrated under vacuum at 80° C.

to remove solvent and any other volatile components. A brown viscous residue was obtained weighing 2.2 grams. $^{1}$H, $^{19}$F and FTIR spectroscopic analysis identified the product as the desired title polymer. Gel permeation chromatographic analysis in methyl ethyl ketone revealed a bimodal molecular weight(MW) distribution in which 59% of the product had a number average MW of 19,670 (P.I.=1.09) and 41% of the product had a number average MW of 4,240 (P.I.=1.12). End group analysis by $^{19}$F NMR indicated that the overall number average MW was 1,860 and that the polymer chains were terminated with sulfonamide and sulfonate end groups. The lower than expected MW is attributed to partial hydrolysis of the sulfonyl fluoride groups by trace amounts of water in the reaction mixture.

The method shown in the Examples uses relatively inexpensive reagents and provides high yields of imides in a single step, i.e. without the isolation of intermediate reaction products. Furthermore, the method allows unsymmetrical imides (imides having two different fluoroalkyl sulfonyl groups, or fluorosulfonyl groups) to be prepared. The method also allows the preparation of polymeric imides from imides having a polymerizable functional group. The imides prepared using the method of this invention may be used, for example, as electrolytes in fuel cells and batteries and as catalysts for polymerization and esterification.

What is claimed is:

1. A process for the preparation of a bis(fluoroalkylsulfonyl)imide salt comprising the step of reacting at least two equivalents of a fluoroalkylsulfonyl halide (wherein the fluoroalkyl is substantially fluorinated) with one equivalent of ammonia and at least three equivalents of a non-nucleophilic base at a temperature and for a time sufficient to yield the imide salt, provided that if the fluoroalkylsulfonyl halide is a perfluoroalkylsulfonyl halide, the alkyl group has at least 2 carbon atoms.

2. The process of claim 1 where the ammonia is generated in situ by the reaction of an ammonium salt with a non-nucleophilic base.

3. The process of claim 1 characterized by the reaction scheme

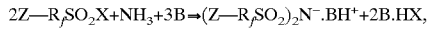

where $R_f$ is a fluoroalkylene group optionally containing catenary oxygen or nitrogen, X is a halogen atom, B is a non-nucleophilic base, and Z is a fluorine atom or a polymerizable organic functional group.

4. The process of claim 3 further comprising contacting the bis(fluoroalkylsulfonyl)imide salt with an inorganic base having an alkali metal cation M$^+$, volatilizing the non-nucleophilic base B, and isolating the resulting bis(fluoroalkylsulfonyl)imide salt of the formula $(Z-R_fSO_2)_2N^-.M^+$ by filtration, evaporating volatile components from the residue, followed by solvent extraction of the filtrate and removal of the solvent.

5. A process for preparing a bis(fluoroalkylsulfonyl)imide which comprises contacting a sulfonamidofluoroalkylenesulfonyl halide of the formula $X-SO_2-R_f-SO_2NH_2$ with a non-nucleophilic base at a temperature and for a time sufficient to produce a polymeric fluoroalkylsulfonimide having the repeat unit $-(SO_2-R_f-SO_2N^-)_n$, wherein n is an integer greater than 1 and X is a halogen atom.

6. A process for preparing a polymeric fluoroalkylsulfonimide comprising a reaction step characterized by the reaction scheme:

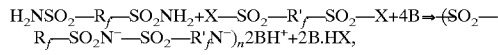

wherein n is an integer greater than 1 and X is a halogen atom.

7. A process for preparing a polymeric fluoroalkylsulfonimide comprising a reaction step characterized by the reaction scheme:

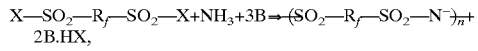

wherein n is an integer greater than 1, $R_f$ is a fluoroalkylene group, B is a non-nucleophilic base and X is a halogen atom.

8. The process of claim 7 wherein the ammonia is generated in-situ by the reaction of an ammonium salt with a non-nucleophilic base.

* * * * *

UNITED STATES PATENT AND TRADEMARK OFFICE
CERTIFICATE OF CORRECTION

PATENT NO.   : 5,874,616
DATED        : February 23, 1999
INVENTOR(S)  : Richard D. Howells, William M. Lamanna, Alan D. Fanta, and Jennifer Waddell It is certified that error appears in the above-identified patent and that said Letters Patent is hereby corrected as shown below:

Title page,
Item [22], "577,425" should read -- 08/577,425 --;

Item [54], "(FLUOROALKYSULFONY)" should read -- (FLUOROALKYSULFONYL) --;

Item [63], "398,859" should read -- 08/398,859 --;

Column 1,
Line 3, "(FLUOROALKYSULFONY)" should read -- (FLUOROALKYSULFONYL) --;

Column 2,
Line 16, "in situ" should read -- *in situ* --;
Line 37, "in situ" should read -- *in situ* --;
Lines 47 and 48, "according the method" should read -- according to the method --;

Column 3,
Line 15, "R©$_f$" should read -- R'$_f$ --;
Line 28, "in situ" should read -- *in situ* --;
Line 48, "5" should be deleted;

Column 5,
Line 39, "in situ" should read -- *in situ* --;

Column 10,
Line 66, "stirring 24 hours" should read -- stirring for 24 hours --;

Column 14,
Line 42, "2($C_2H_5$)$_3$NH+]$_n$" should read -- • "2($C_2H_5$)$_3$NH+]$_n$ --;

UNITED STATES PATENT AND TRADEMARK OFFICE
CERTIFICATE OF CORRECTION

PATENT NO. : 5,874,616
DATED : February 23, 1999
INVENTOR(S) : Richard D. Howells, William M. Lamanna, Alan D. Fanta, and Jennifer Waddell It is certified that error appears in the above-identified patent and that said Letters Patent is hereby corrected as shown below:

Column 15,
Line 37, "in situ" should read -- *in situ* --;

Column 16,
Line 11, "residue" should read -- filtrate --; and "filtrate" should read -- residue --;
Line 25, "$_n$2BH+" should read -- $_n$2BH+ --; and
Line 39, "in situ" should read -- *in situ* --;

Signed and Sealed this

Eighth Day of January, 2002

Attest:

JAMES E. ROGAN
Attesting Officer   Director of the United States Patent and Trademark Office